United States Patent [19]
Williamson, Jr.

[11] Patent Number: 5,769,092
[45] Date of Patent: Jun. 23, 1998

[54] COMPUTER-AIDED SYSTEM FOR REVISION TOTAL HIP REPLACEMENT SURGERY

[75] Inventor: Willie Williamson, Jr., Roseville, Calif.

[73] Assignee: Integrated Surgical Systems, Inc., Sacramento, Calif.

[21] Appl. No.: 606,989

[22] Filed: Feb. 22, 1996

[51] Int. Cl.[6] .................................................. A61B 19/00
[52] U.S. Cl. .......................... 128/898; 600/425; 600/427; 128/922; 128/923
[58] Field of Search .................................... 128/898, 922, 128/923; 364/413.13; 623/16, 66; 600/425, 427

[56] References Cited

U.S. PATENT DOCUMENTS

| 4,436,684 | 3/1984 | White .................................. 600/427 X |
| 5,086,401 | 2/1992 | Glassman et al. ........................ 395/94 |
| 5,192,283 | 3/1993 | Ling et al. .................................. 606/93 |
| 5,299,288 | 3/1994 | Glassman et al. ........................ 395/80 |
| 5,408,409 | 4/1995 | Glassman et al. .................. 364/413.13 |

OTHER PUBLICATIONS

Mittelstadt et al. "Development of a surgical robot for cementless total hip replacement." Robotics 11:553–560, 1993.

*Primary Examiner*—Aaron J. Lewis
*Assistant Examiner*—Kelly O'Hara
*Attorney, Agent, or Firm*—Townsend and Townsend and Crew LLP

[57] ABSTRACT

Computer implemented systems and methods for removing bone cement or other material to replace a bone prosthesis is provided. A computer aided method of replacing a bone prosthesis according to the present invention comprises the steps of: receiving as input image data of a bone; identifying bounding contours of material in the image data surrounding a first bone prosthesis for removal; and generating system contours from the bounding contours, the system contours specifying a cavity to be cut in the bone to accommodate a second bone prosthesis.

12 Claims, 12 Drawing Sheets

COMPUTER-AIDED SYSTEM FOR REVISION TOTAL HIP REPLACEMENT SURGERY

COPYRIGHT NOTICE

A portion of the disclosure of this patent document contains material which is subject to copyright protection. The copyright owner has no objection to the xerographic reproduction by anyone of the patent document(s) or the patent disclosure in exactly the form it appears in the Patent and Trademark Office patent file or records, but otherwise reserves all copyrights whatsoever.

BACKGROUND OF THE INVENTION

1. Field of the Invention

The present invention relates to the field of computer-aided surgical systems and methods. More specifically, the present invention provides a computer-aided system and method for performing revision total hip replacement surgery.

Total hip replacement (THR) surgery (also called primary total hip arthroplasty) is a surgical procedure where a surgeon replaces a patient's ball-and-socket joint with a prosthetic device. The prosthetic device includes an acetabular cup and a femoral prosthesis. The femoral prosthesis provides the replacement "ball" and the acetabular cup provides the replacement "socket" of the ball-and-socket joint. Thousands of people today are able to retain their desired mobility and have reduced pain because of total hip replacement surgery.

Figure 1:
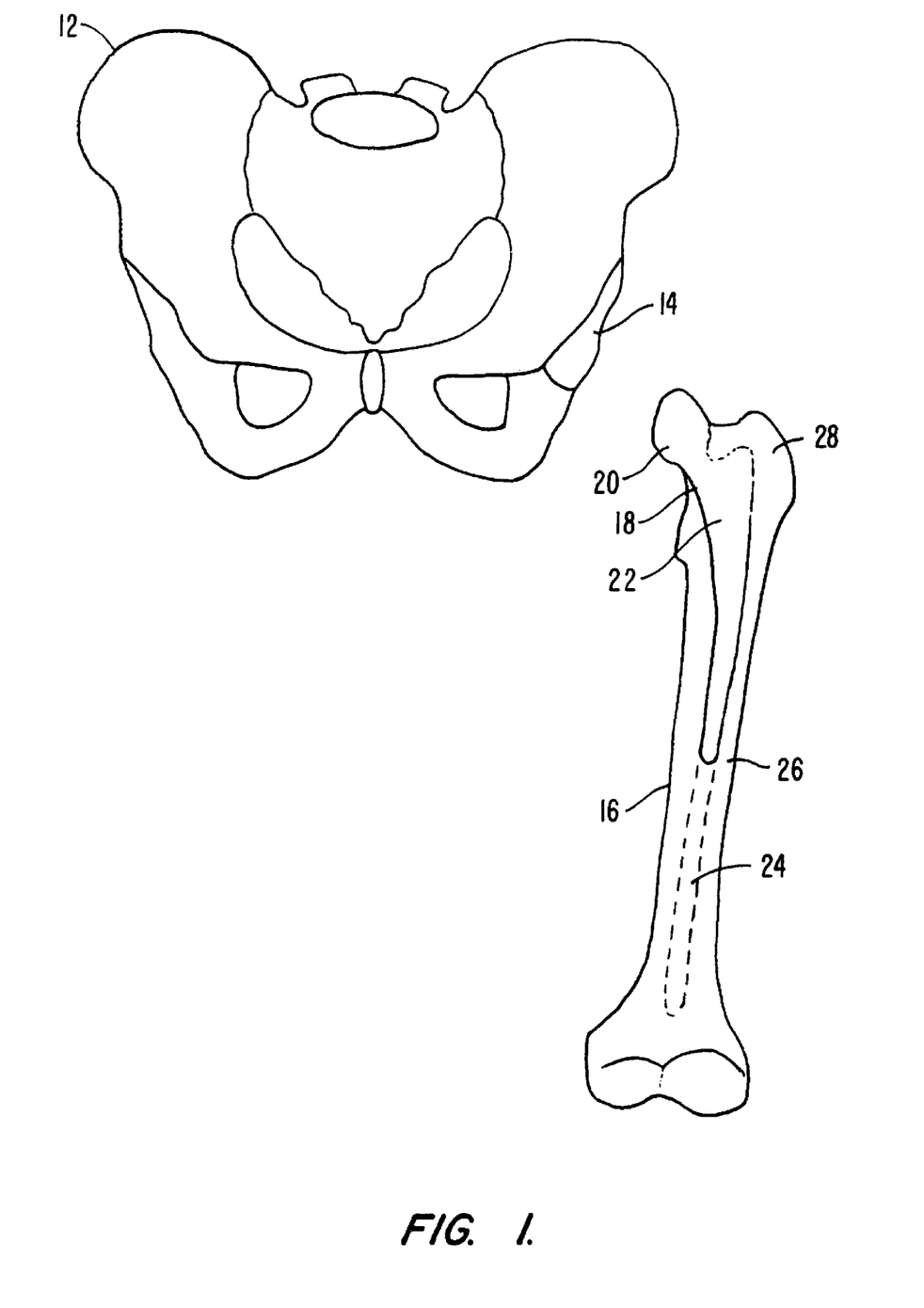
FIG. 1 shows total hip replacement surgery prostheses.

FIG. 1 shows total hip replacement surgery prostheses. A pelvis 12 has been implanted with an acetabular cup 14. A corresponding femur 16 has been implanted with a femoral prosthesis 18. The femoral prosthesis includes a femoral head 20 and a femoral stem 22. The surgeon implants the femoral prosthesis by first removing the bone femoral head and then excavating to and extending the femoral canal 24 within the femur so that the femoral stem may be placed in the femoral canal adjacent to the cortical bone 26. Once the femoral prosthesis is implanted, the femoral head of the prosthesis is adjacent to the trabecular bone 28.

Surgeons typically prepare a cavity for the femoral stem with inaccurate methods. Reamers (hand-held drills) and broaches (serrated cutting tools) are utilized by surgeons to produce the femoral cavity. Laboratory tests have shown that the cavities produced by these methods are irregular, resulting in relatively large gaps between the bone and the prosthesis. These gaps may result when the broach tears out chunks of trabecular bone instead of making a precise cut. Additionally, the gaps may be caused by the tendency of a broach to cut the material with the least resistance when it makes contact with dense trabecular or cortical bone. Bone cement (polymethylmethacrylate or PMMA) is typically utilized to fill in the gaps between the femur and the femoral prosthesis.

The prosthetic device utilized in THR surgery has a limited life expectancy and therefore, at times, may need to be replaced. The replacement of the prosthetic device is called revision total hip replacement (RTHR) surgery (also called revision total hip arthroplasty). When replacing the femoral prosthesis, the old femoral prosthesis must be removed and it is desirable to remove all or much of the bone cement from within the femoral canal (e.g., there may be a structural failure of the bone cement). One of the most difficult aspects of RTHR surgery is that the surgeon may have very limited information about the location and amount of bone cement in the femur during the surgical procedure.

Possibly the most frequently used method of removing bone cement during RTHR surgery involves utilizing hand tools. A large variety of osteotomes, cement splitters, hooks, and threaded cement taps are available for this technique. However, this technique is tedious and becomes progressively more difficult as deeper bone cement is removed because the surgeon has reduced visibility. Additionally, the surgeon must use extreme caution to avoid fracturing or perforating the femur.

In order to increase visibility, holes or windows may be drilled or cut in the cortical bone. Although this technique allows greater visualization, the holes or windows further weaken the femur and increase the risk of fracturing the femur. Other techniques include utilizing ultrasound or laser energy to remove the bone cement but these techniques may provide the surgeon with limited visualization of the bone cement.

Revision total hip replacement surgery is an extremely challenging surgical procedure that is often accompanied by an equally challenging set of problems. For example, complications during bone cement removal may result in cortical wall penetration or bone fracture. Additionally, good bone within the femur may be unnecessarily sacrificed to fit the new prosthesis. The new femoral canal created may be irregular, thereby propagating the problems associated with the first prosthesis. Also, the time and expense of bone cement removal may be significant.

Recently, innovative systems have been developed for performing robot assisted total hip replacement surgery. The ORTHODOC™ presurgical planning workstation developed by Integrated Surgical Systems, Inc., Sacramento, Calif., assignee of the present application, allows the surgeon to plan the placement of the femoral prosthesis on a workstation utilizing an image of the femur, typically a computerized tomography (CT) scan image. Once placement of the implant has been planned, the workstation generates data for use by a computer-controlled robotic system intended to perform the surgery, such as the ROBODOC™ surgical robot system which is also developed by Integrated Surgical Systems.

It would be desirable to provide improved systems and methods for performing revision total hip replacement surgery. It would be particularly desirable to provide systems and methods for performing revision total hip replacement surgery that reduce morbidity and surgical complication rates, retain as much of the femoral bone as possible, shorten surgery time and hospital stays, and reduce overall costs.

2. Description of the Background Art

Conventional techniques for bone cement removal in revision total hip replacement surgery are described in (1) Lombardi, Jr., A.: "Cement Removal in Revision Total Hip Arthroplasty," *Seminars in Arthroplasty*, Volume 3, No. 4, Pages 264–272, Oct. 1992.

The ORTHODOC™ presurgical planning workstation and the ROBODOC™ robotic surgical system are described in a number of references, including the following: (2) Kazanzides, P., Zuhars, J., Mittelstadt, B. D., Taylor, R. H.: "Force Sensing and Control for a Surgical Robot," *Proc. IEEE Conference. on Robotics & Automation*, Pages 612–616, Nice, France, May 1992. (3) Kazanzides, P., Zuhars, J., Mittelstadt, B. D., Williamson, B., Cain, P., Smith, F., Rose, L., Mustis, B.: "Architecture of a Surgical Robot," *Proc. IEEE Conference. on Systems, Man, and Cybernetics*, Chicago, Ill. Pages 1624–1629, October 1992.

(4) Paul, H. A., Bargar, W. L., Mittelstadt, B., Musits, B., Taylor, R. H., Kazanzides, P., Zuhars, J., Williamson, B., Hanson, W.: "Development of a Surgical Robot For Cementless Total Hip Arthroplasty," *Clinical Orthopaedics*, Volume 285, Pages 57–66, December 1992. (5) Kazanzides, P., Mittelstadt, B. D., Zuhars, J., Cain, P., Paul, H. A., "Surgical and Industrial Robots: Comparison and Case Study," *Proc. International Robots and Vision Automation Conference*, Pages 1019–1026, Detroit, Mich. April 1993. (6) Mittelstadt, B., Kazanzides, P., Zuhars, J., Williamson, B., Pettit, R., Cain, P., Kloth, D., Rose, L., Musits, B.: "Development of a surgical robot for cementless total hip replacement," *Robotica*, Volume 11, Pages 553–560, 1993. (7) Mittelstadt B., Kazanzides, P., Zuhars, J., Cain, P., Williamson, B.:"Robotic surgery: Achieving predictable results in an unpredictable environment," *Proc. Sixth International Conference on Advanced Robotics*, Pages 367–372, Tokyo, November, 1993. (8) Cain, P., Kazanzides, P., Zuhars, J., Mittelstadt, B., Paul, H.: "Safety Considerations in a Surgical Robot," *Biomedical Sciences Instrumentation*, Volume 29, Pages 291–294, San Antonio, Tex. April 1993. (9) Mittelstadt, B. D., Kazanzides, P., Zuhars, J., Williamson, B., Cain, P., Smith, F. Bargar, W.: "The Evolution of A Surgical Robot From Prototype to Human Clinical Use," in *Proc. First International Symposium on Medical Robotics and Computer Assisted Surgery*, Volume I, Pages 36–41, Pittsburgh, Pa. September 1994.

Other publications which describe image registration in robotic surgical and other procedures include the following: (10) Grimson, W. E. L., Lozano-Pérez, T., Wells III, W. M., Ettinger, G. J., White, S. J., Kikinis, R.: "Automated Registration for Enhanced Reality Visualization in Surgery," *Proceedings of the First International Symposium on Medical Robotics and Computer Assisted Surgery*, Volume I, Sessions I-III, Pages 82–89, Pittsburgh, Pa. Sep. 22–24, 1995. (11) Nolte, L. P., Zamorano, L. J., Jiang, Z., Wang, Q., Langlotz, F., Arm, E., Visarius, H.: "A Novel Approach to Computer Assisted Spine Surgery," *Proceedings of the First International Symposium on Medical Robotics and Computer Assisted Surgery*, Volume II, Session IV, Pages 323–328, Pittsburgh, Pa., Sep. 22–24, 1994. (12) Lavallée, S., Sautot, P., Troccaz, J., Cinquin, P., Merloz, P.: "Computer Assisted Spine Surgery: a technique for accurate transpedicular screw fixation using CT data and a 3-D optical localizer," *Proceedings of the First International Symposium on Medical Robotics and Computer Assisted Surgery*, Volume II, Session IV, Pages 315–321, Pittsburgh, Pa., Sep. 22–24, 1994. (13) Potamianos, P., Davies, B. L., Hibberd, R. D.: "Intra-Operative Imaging Guidance For Keyhole Surgery Methodology and Calibration," *Proceedings of the First International Symposium on Medical Robotics and Computer Assisted Surgery*, Volume I, Sessions I-III, Pages 98–104, Pittsburgh, Pa. Sep., 22–24, 1994. (14) Simon, D. A., Hebert, M., Kanade, T.: "Techniques for Fast and Accurate Intra-Surgical Registration," *Proceedings of the First International Symposium on Medical Robotics and Computer Assisted Surgery*, Volume I, Sessions I-III, Pages 90–97, Pittsburgh, Pa., Sep. 22–24, 1995. (15) Péria, O., Francois-Joubert, A., Lavallée, S., Champleboux, G., Cinquin, P., Grand, S.: "Accurate Registration of SPECT and MR brain images of patients suffering from epilepsy or tumor," *Proceedings of the First International Symposium on Medical Robotics and Computer Assisted Surgery*, Volume II, Session IV, Pages 58–62, Pittsburgh, Pa. Sep. 22–24, 1995. (16) Lea, J. T., Watkins, D., Mills, A., Peshkin, M. A., Kienzle III, T. C., Stulberg, D. S.: "Registration and Immobilization for Robot-Assisted Orthopaedic Surgery," *Proceedings of the First International Symposium on Medical Robotics and Computer Assisted Surgery*, Volume I, Sessions I-III, Pages 63–68, Pittsburgh, Pa. Sep. 22–24, 1995. (17) Ault, T., Siegel, M. W.: "Frameless Patient Registration Using Ultrasonic Imaging," *Proceedings of the First International Symposium on Medical Robotics and Computer Assisted Surgery*, Volume I, Sessions I-III, Pages 74–81, Pittsburgh, Pa. Sep. 22–24, 1995. (18) Champleboux, G., Lavallée, S., Cinquin, P.: "An Optical Conformer for Radiotherapy Treatment Planning," *Proceedings of the First International Symposium on Medical Robotics and Computer Assisted Surgery*, Volume I, Sessions I-III, Pages 69–73, Pittsburgh, Pa. Sep. 22–24, 1995.

A system and method for performing robotically o assisted surgery is described in U.S. Pat. No. 5,086,401. Computer-assisted imaging and probe tracking systems are described in U.S. Pat. No. 5,383,454; U.S. Pat. No. 5,198,877; and WO 91/07726.

SUMMARY OF THE INVENTION

The present invention provides computer implemented systems and methods for removing bone cement or other material to replace a bone prosthesis, typically a bone prosthesis utilized in hip replacement surgery, knee replacement surgery, and the like. A computer aided method of replacing a bone prosthesis according to the present invention comprises the steps of: receiving as input, image data of a bone; identifying bounding contours of material in the image data surrounding a first bone prosthesis for removal; and generating system contours from the bounding contours, the system contours specifying a cavity to be cut in the bone to accommodate a second bone prosthesis. The cavity may be cut or machined by a surgical robot.

In one embodiment, a computer aided method of replacing a bone prosthesis according to the present invention comprises the steps of: imaging a bone to produce image data; identifying bounding contours of material in the image data surrounding a first bone prosthesis for removal; generating system contours from the bounding contours, the system contours specifying a cavity to be cut in the bone to accommodate a second bone prosthesis; cutting the cavity specified by the system contours; and implanting the second bone prosthesis in the cavity.

Other features and advantages of the present invention will become readily apparent upon a perusal of the following description and accompanying drawings.

DETAILED DESCRIPTION OF THE SPECIFIC EMBODIMENTS

The present invention provides computer implemented systems and methods for replacing a bone prosthesis, especially a femoral prosthesis in revision total hip replacement surgery. The present invention allows a surgeon to plan the placement of the new femoral prosthesis in an interactive work environment. In the interactive work environment, the surgeon may identify bone cement, create a custom cutting strategy for removal of the cement, evaluate the stability of the remaining bone, minimize the amount of bone removed, and verify that the new implant will be insertable in the new femoral cavity.

Figure 2:
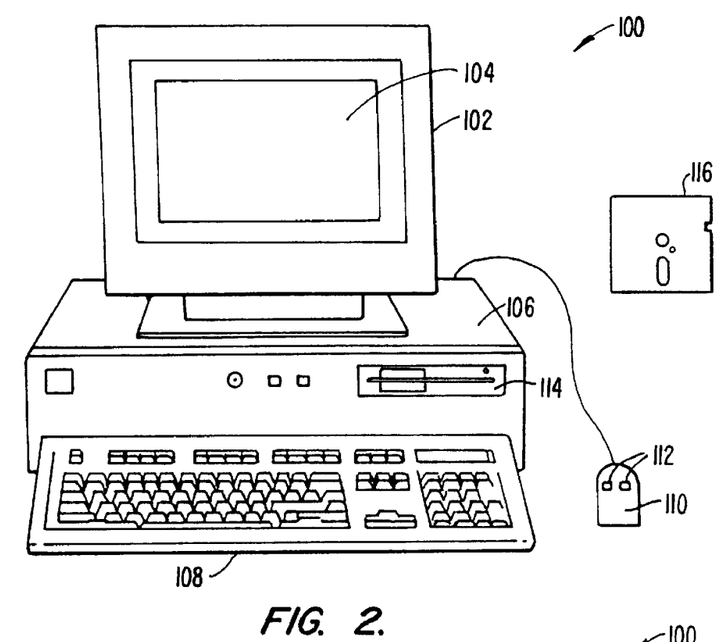
FIG. 2 illustrates an example of a computer system capable of executing the software of the present invention.

FIG. 2 illustrates an example of a computer system capable of executing the software of the present invention. FIG. 2 shows a computer system 100 which includes a monitor 102, display screen 104, cabinet 106, keyboard 108, and mouse 110. Mouse 110 may have one or more buttons such as mouse buttons 112. Cabinet 106 houses a floppy drive 114 or a hard drive (not shown) which may be utilized to store and retrieve the computer readable code of software programs incorporating the present invention, patient information, image data of bones, files defining cutting contours, and the like. Although a floppy diskette 116 is shown as the removable media, other removable tangible media including CD-ROM, tape, and flash memory may be utilized. Cabinet 106 also houses familiar computer components (not shown) such as a processor, memory, and the like.

Figure 3:
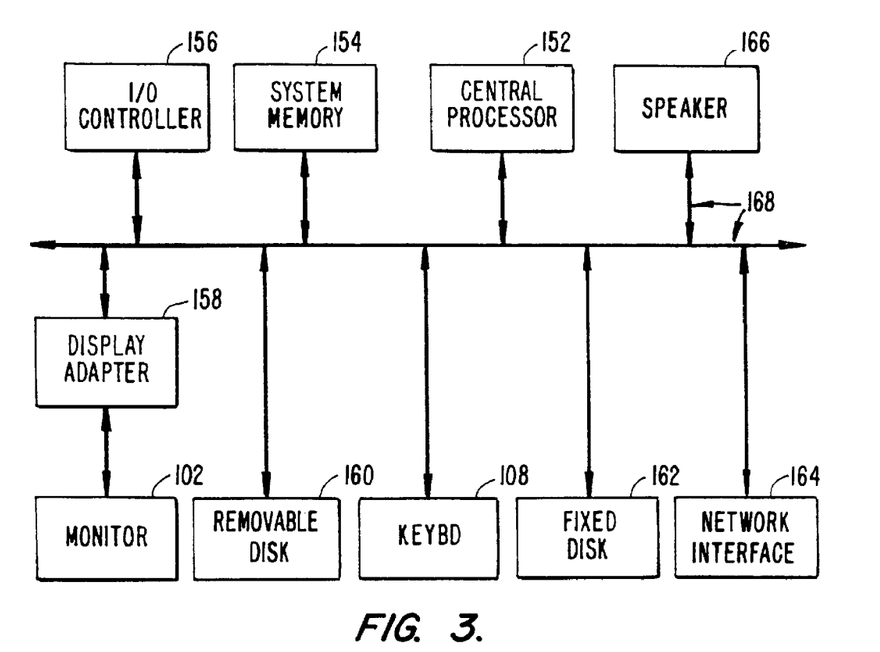
FIG. 3 shows a system block diagram of a typical computer system.

FIG. 3 shows a system block diagram of computer system 100. As in FIG. 2, computer system 100 includes monitor 102 and keyboard 108. Computer system 100 further includes subsystems such as a central processor 152, system memory 154, I/O controller 156, display adapter 158, removable disk 160, fixed disk 162, network interface 164, and speaker 166. Other computer systems suitable for use with the present invention may include additional or fewer subsystems. For example, another computer system could include more than one processor 102 (i.e., a multi-processor system) or a cache memory.

Arrows such as 168 represent the system bus architecture of computer system 100. However, these arrows are illustrative of any interconnection scheme serving to link the subsystems. For example, a local bus could be utilized to connect the central processor to the system memory and display adapter. Computer system 100 shown in FIG. 3 is but an example of a computer system suitable for use with the present invention. Other configurations of subsystems suitable for use with the present invention will be readily apparent to one of ordinary skill in the art.

In a preferred embodiment, the present invention operates on an IBM RS/6000 computer running the UNIX operating system. However, the invention is not limited to any computer architecture or operating system and the description of the embodiments that follows is for purposes of illustration and not limitation.

Figure 4:
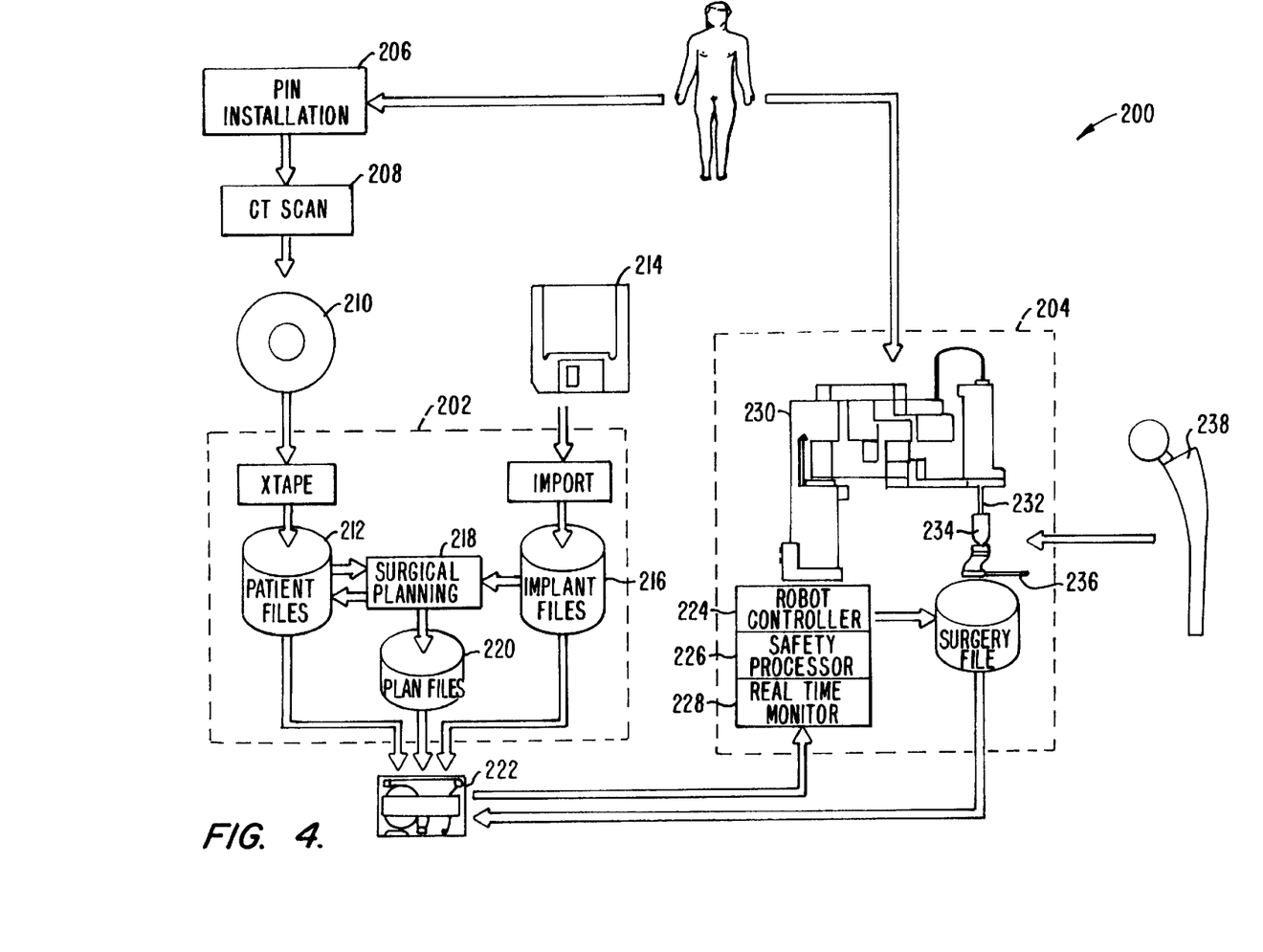
FIG. 4 illustrates an architecture of a robotic surgical system including a presurgical planning component and a surgical component.

FIG. 4 illustrates an architecture of a robotic surgical system including a presurgical planning component and a surgical component which are capable of implementing the methods of the present invention. A system 200 for revision total hip replacement surgery may include both a presurgical planning workstation 202 and a surgical robot system 204. In a preferred embodiment, the presurgical planning workstation is the ORTHODOC™ presurgical planning workstation which includes an IBM RS/6000 computer. In a preferred embodiment, the surgical robot system is the ROBODOC™ surgical robot system. The following will describe the present invention in reference to a preferred embodiment utilizing the ORTHODOC™ presurgical planning workstation and the ROBODOC™ surgical robot system. However, other systems may be utilized and therefore this description is for purposes of illustration and not limitation.

For alignment of the femur, the surgical robot system relies on the surgical implantation of a pair of metallic pins on the distal (lower) end of the femur and one additional metallic pin in the proximal end of the bone. These pins are readily apparent in the CT image of the bone and can thus be relied on to register the bone image with the robotic coordinate space by engaging a probe placed on the manipulator arm against each of the pins. Accordingly, prior to surgery, pin installation 206 will be performed followed by a CT scan 208. The image data from the CT scan is stored on a magnetic tape 210. Presurgical planning workstation 202 reads the CT scan data and stores it in a database of patient files 212. Although the present invention will be described as utilizing a CT scan, other imaging techniques may be utilized including x-rays.

Implant designs of different femoral prostheses may be stored on a floppy disk 214. The implant designs are typically in the form of computer aided design (CAD) models which may be available from the manufacturers. Presurgical planning workstation 202 reads the implant designs and stores them in a database of implant files 216. The presurgical planning workstation utilizes data from the patient files and implant files to allow a surgeon to perform surgical planning 218 of the revision total hip replacement. Details of the surgical planning will be described in more detail below. Surgical planning generates plan files 220 which may include a cut binary file and a check volume file. The plan files may be placed on a digital tape 222 for use by the surgical robot system.

Surgical robot system 204 includes a robotic controller 224 (typically a digital processor in the form of a programmable computer), a safety processor 226, a real time monitor computer 228, and a robot 230. The robot can be any conventional industrial robot having a manipulatable arm 232 preferably having at least 5 axes and capable of high precision placement. A suitable robotic is available from Sankyo Robotics with the model designation SR-5427-ISS. For use in the present invention, a force sensor 234 is mounted at the distal end of arm 232, and an effector in the form of a probe 236 or a surgical cutting tool (not shown) may be attached to the force sensor to cut a cavity for a femoral prosthesis 238.

The surgical robot system further includes a display monitor and a bone motion monitor (both not shown). The force sensor, safety processor, real time monitor, and bone motion monitor, each help monitor the position, slippage, and blockage of the effector end of the manipulatable arm 232 while the femur is held in place in a fixator assembly (not shown). Real time monitoring of these parameters helps assure that the robotic system is operating as planned. Details of these monitoring systems are described in the literature cited above which describes the ROBODOC™ robotic surgical system.

Figure 5:
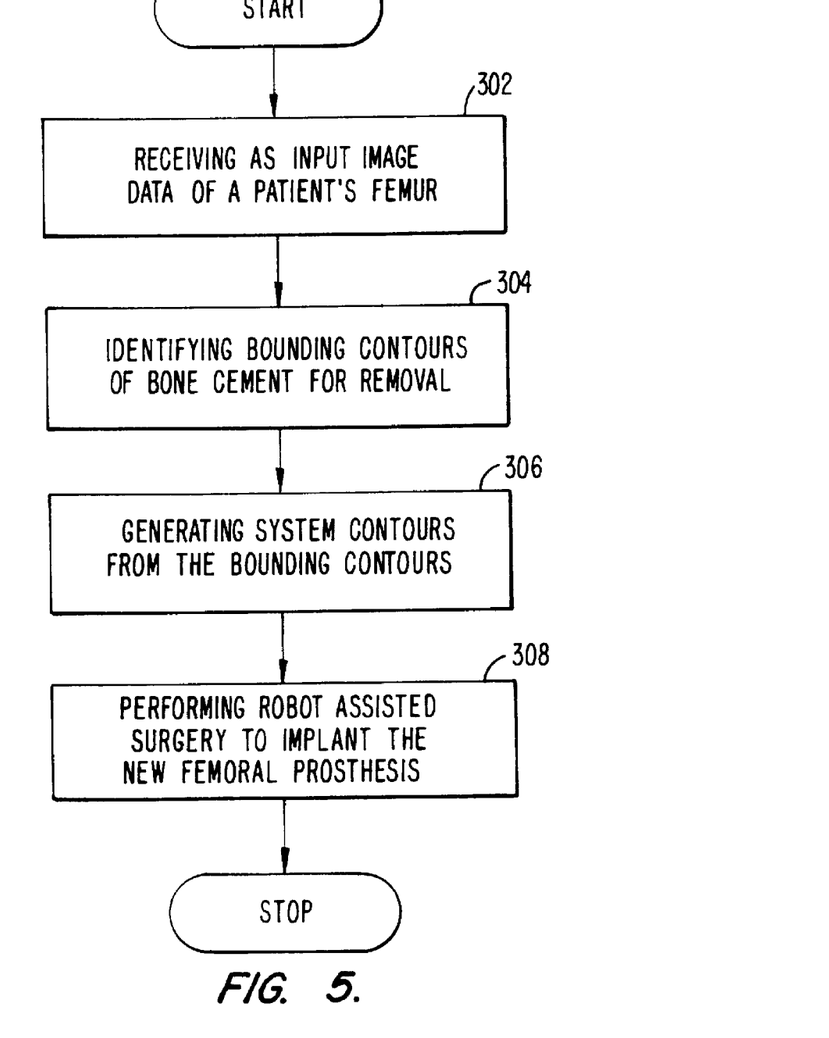
FIG. 5 shows a high level flowchart of performing revision total hip replacement surgery.

FIG. 5 shows a high level flowchart of performing revision total hip replacement surgery. The flowchart of FIG. 5 is at a high level to give the reader a broad overview of the present invention. More detailed aspects of the present invention will be discussed in reference to the figures that follow. At step 302, the system receives as input image data of a patient's femur. The image data may be a CT scan, x-ray, and the like. Utilizing the image data, the system displays multiple views of the femur on the display screen. The surgeon is then able to select a new femoral prosthesis and determine the placement of the implant utilizing the multiple views. Once the surgeon is satisfied with the fit and placement of the new implant, cement removal may be planned.

At step 304, the surgeon identifies bounding contours of bone cement (or other material) for removal. The term "bounding contour" refers to the user selected (or computer selected) region that bounds the bone cement. The bounding contours are not necessarily an exact outline of the bone cement, instead, they more commonly define a region that bounds the bone cement. In a preferred embodiment, the bounding contours are defined by a user selecting points bounding the bone cement on a cross-section transverse to the axis of the femur. However, the computer may be utilized to present the user with an initial estimate of the bounding contours.

The system generates system contours from the bounding contours at step 306. The term "system contour" refers to the computer generated region that represents the cut cavity for the new prosthesis. The system generates the system contours by analyzing the bounding contours and determining if the robot can machine or cut the cavity defined by the bounding contours. If the system determines that the robot will not be able to machine the cavity, the system varies the system contours so that the cavity may be machined by the robot.

The previous steps are part of presurgical planning for the revision total hip replacement surgery. At step 308, robot assisted surgery is performed to implant the new femoral prosthesis. During surgery, the surgeon initially exposes the femur and attaches the robot to the femur. The robot then machines the new cavity to remove the bone cement and prepare for the new implant. After the cavity is machined, the surgeon implants the new femoral prosthesis and closes the incision.

Figure 6A:
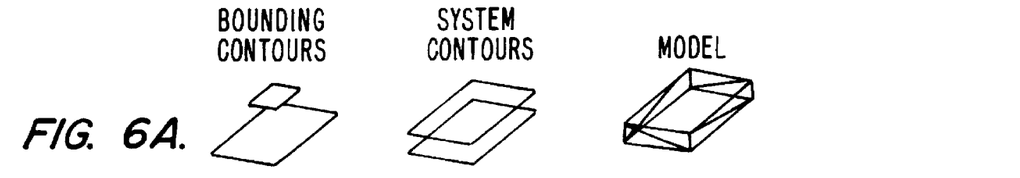
FIG. 6 illustrates examples of bounding contours, system contours and three-dimensional (3D) contour models.
Figure 6B:
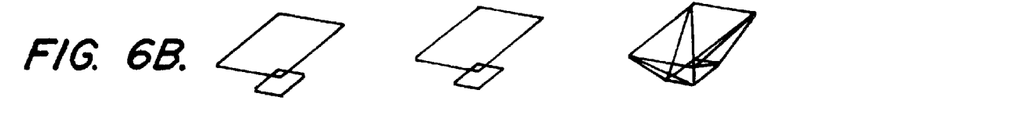

FIG. 6 shows two examples of bounding contours, system contours and 3D contour models. In FIG. 6, the cavity will be cut from top to bottom and the bounding contours define regions at different depths that bound the bone cement. In example A, the system analyzes the bounding contours and determines that the system contour at the first depth will have to be larger than the corresponding bounding contour in order to allow the surgical robot to machine the cavity. The 3D contour model shows a three-dimensional representation of the cavity that will be cut.

In example B, the system analyzes the bounding contours and determines that the system contours do not need to be varied from the bounding contours to allow the surgical robot to machine the cavity. The 3D contour model again shows a three-dimensional representation of the cavity that will be cut. The system may analyze differ cutter angles to determine if the cavity defined by the bounding contours can be machined.

Figure 7:
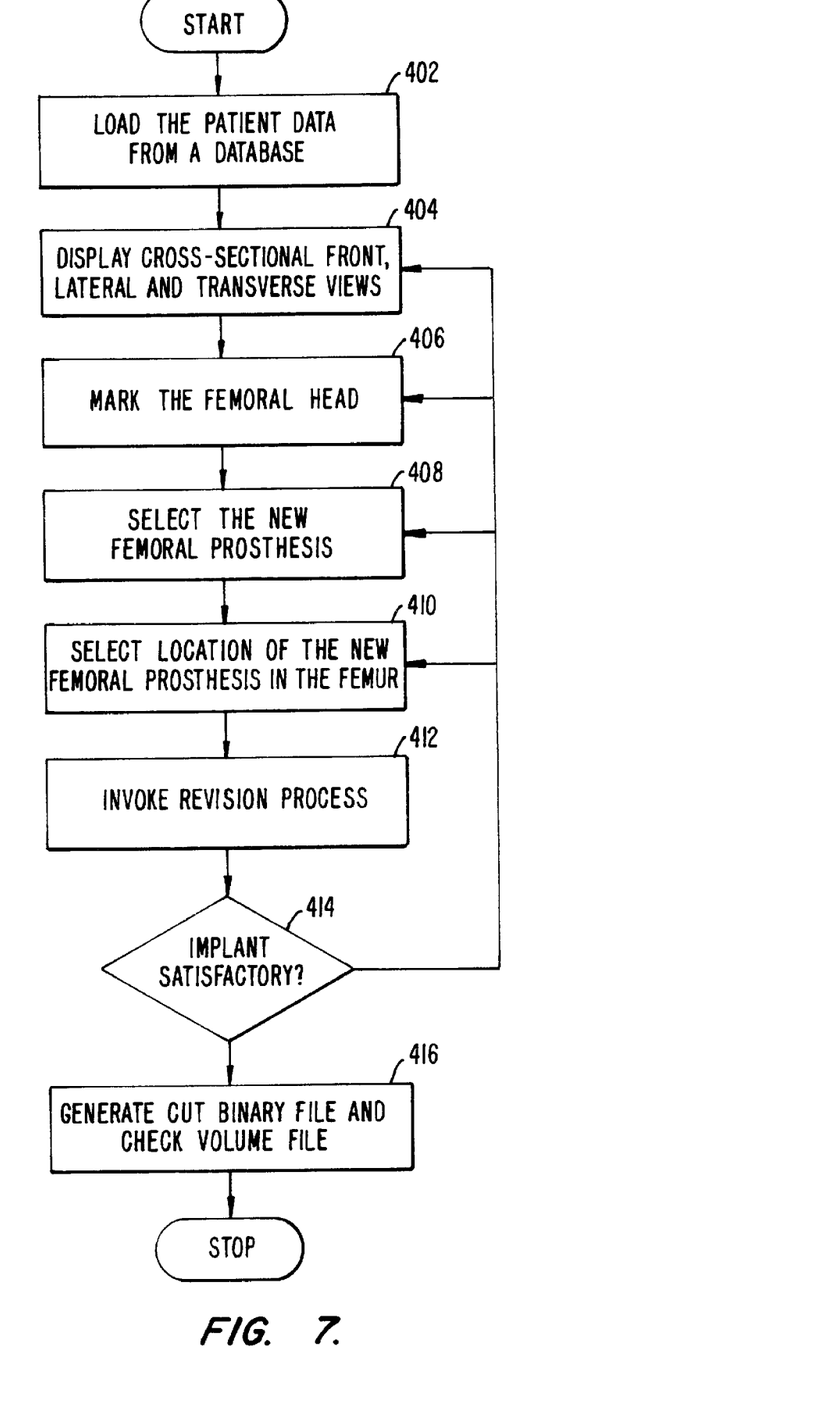
FIG. 7 shows a high level flowchart of a process of generating plan files specifying the removal of bone cement.

FIG. 7 shows a high level flowchart of a process of generating plan files specifying the removal of bone cement. At step 402, the system loads the patient data from a database. The patient data may include a CT scan image of the patient's femur and other information. The system displays a cross-sectional front, lateral and transverse views on the screen display at step 404.

Figure 8:
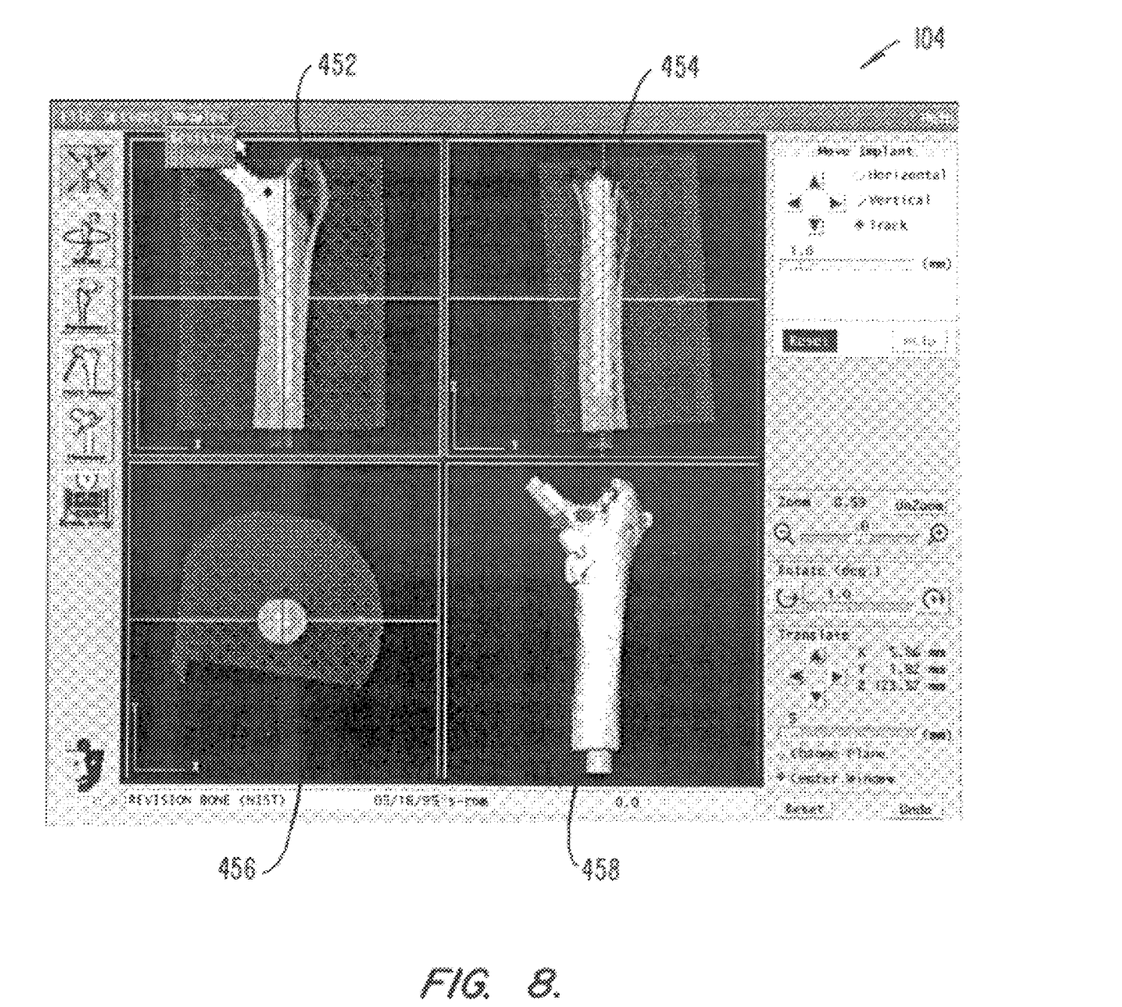
FIG. 8 is a screen display showing a cross-sectional front, lateral and transverse views.

FIG. 8 is a screen display showing a cross-sectional front, lateral and transverse views. Screen display 104 includes a cross-sectional front view 452, lateral view 454 and transverse view 456. Additionally, the screen display includes a 3D view 458.

Referring again to FIG. 7, the surgeon marks the femoral head or implant head on the screen display at step 406. The surgeon may mark the femoral head of the old femoral prosthesis. The marked femoral head may then be utilized to align views of the femur. Additionally, the marked femoral head may give a user a guide to proper implant rotation during implantation.

The surgeon or user selects the new femoral prosthesis from a database at step 408. Once the new prosthesis is chosen, the user selects the location of the prosthesis in the femur utilizing the multiple views on the display screen. In a view, the user may move the prosthesis vertically, horizontally, or rotate the prosthesis. The other views will be updated to reflect the new position of the prosthesis.

Once the user is satisfied with the selected implant and its location in the femur, the user starts the revision process at step 412. The revision process defines the cavity to be machined by the surgical robot and is invoked by utilizing a pull down menu entry as shown in FIG. 8. The revision process is shown in FIG. 9 which will now be discussed.

Figure 9:
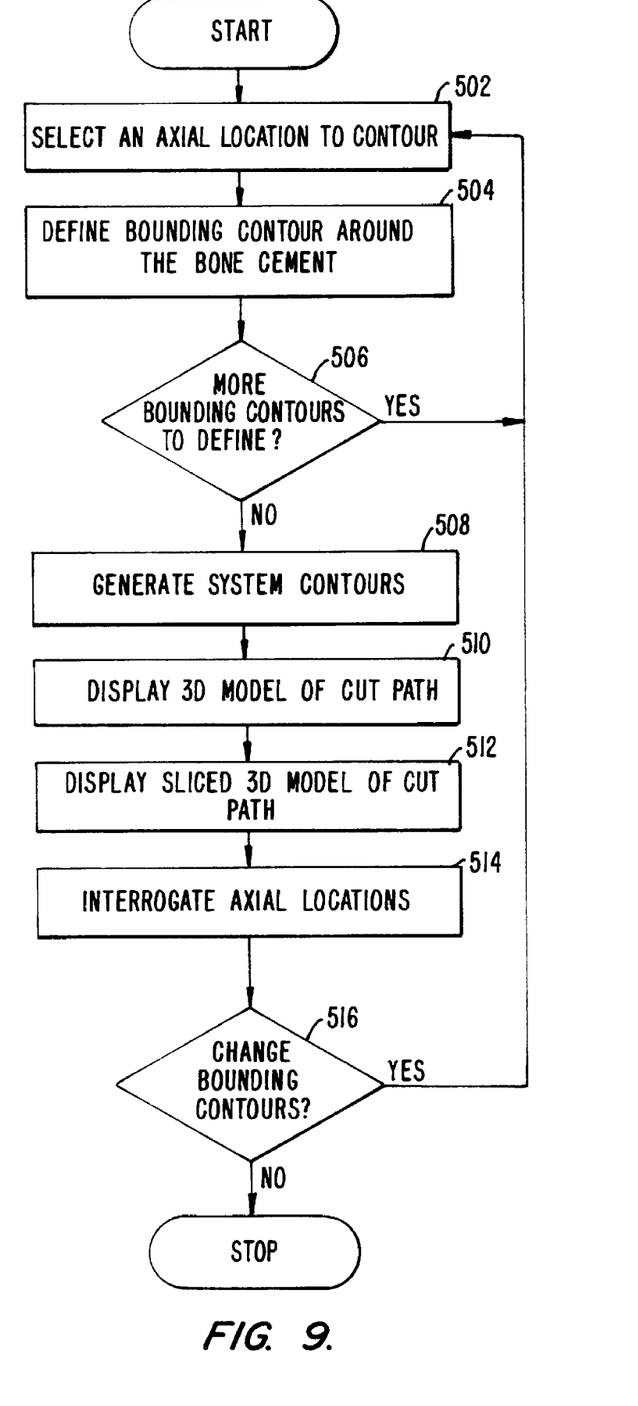
FIG. 9 shows a flowchart of a revision process that defines the cavity to be cut for the new prosthesis.

FIG. 9 shows a flowchart of a revision process that defines the cavity to be cut for the new prosthesis. At step 502, the user selects an axial location to contour. When the user selects an axial location, the system displays a cross-section that is transverse to the axis of the femur. With this cross-section, the user is able to see the amount and location of bone cement that bounds the old implant at this cross-section.

At step 504, the user defines a bounding contour around the bone cement in this cross-section. The user defines bounding contours by selecting points around or on the femur/bone cement interface. The user typically selects many points around the bone cement but the number of points may be determined by a number of factors including the amount of bone cement present in the cross-section, the location of the bone cement, the location of the cross-section along the axis of the femur, and user discretion. In one embodiment, the system first identifies the bone/cement interface and then automatically generates an initial estimation for the bounding contours around the bone cement. The user may then accept these bounding contours or modify the bounding contours.

Once the user is finished defining the bounding contour for a cross-section, the user determines whether more bounding contours are to be defined at step 506. If more bounding contours are to be defined, the user selects another axial location to contour at step 502. Typically, the user selects axial locations in a top-down order from the greater trochanter. However, the user may choose to define bounding contours in any direction or order.

Once the user is done defining the bounding contours, the system generates system contours at step 508. The system contours represent the cut cavity to be machined. The system generates the system contours by analyzing the bounding contours and determining if the robot can machine or cut the cavity defined by the bounding contours. If the system determines that the robot will not be able to machine the cavity, the system varies the system contours so that the cavity may be machined by the robot. In one embodiment, the system also verifies that the new implant will be insertable in the new femoral cavity.

At step 510, the system displays a 3D model of the cut path defined by the system contours. The system also displays a sliced 3D model of the cut path on the cross-sectional views on the display screen at step 512. It should be readily apparent that the order of steps 510 and 512 is not essential and thus, the order of these and other steps may be modified without departing from the scope of the invention. In embodiment, the system displays the bounding contours in one color (e.g., blue) and the system contours in another color (e.g., red) on the cross-sectional views. This allows a user to more easily identify the different contour regions.

The user may interrogate axial locations at step 514. The user may select an axial location that was utilized to form the bounding contours or new axial locations. When the user selects an axial location, the system displays a cross-section that is transverse to the axis of the femur. With this cross-section, the user is able to see the amount and location of bone cement that bounds the old implant at this cross-section with the associated bounding contour (if defined at this axial location) and system contour. If the user desires to change the bounding contours or system contours, the user is able to make this choice at step 516.

A user may interrogate axial locations and modify the existing bounding contours (e.g., adjusting, adding or deleting points that define the bounding contour). Additionally, a user may interrogate axial locations and add new bounding contours at new axial locations. Once a user changes the bounding contours, the changes may affect the system contours that define the cut cavity.

Referring again to FIG. 7, after the revision process, the user indicates whether the cut cavity for the new implant is satisfactory at step 414. If the cut cavity or implant is not satisfactory, the user may return to any number of previous steps. As shown in FIG. 7, the user may return to step 410 where the location of the new femoral prosthesis may be changed. Alternatively, the user may select a different prosthesis at step 408 or other steps.

If the cut cavity and implant are satisfactory, the system generates plan files including the cut binary file and check volume file at step 416. In order to assist the user in determining if the cut cavity and implant are satisfactory, the user may instruct the system to generate a synthetic x-ray where the system removes the old implant and imposes the new cut cavity and implant. In this manner, the user is able to view a simulation of an x-ray of the new implant after the surgery.

The cut binary file is the file that instructs the surgical robot in machining the cavity for the new prosthesis. The check volume file is a file that may include the volume and other characteristics (width, depth, height, and the like) of the cut cavity for safety backup. If the surgical robot attempts to machine a cavity with a volume or characteristics in excess of the values in the check volume file, the surgical robot automatically shuts off. Thus, the check volume file provides an extra safety mechanism intended to prevent the surgical robot from machining a different cavity than the one selected.

Figure 10A:
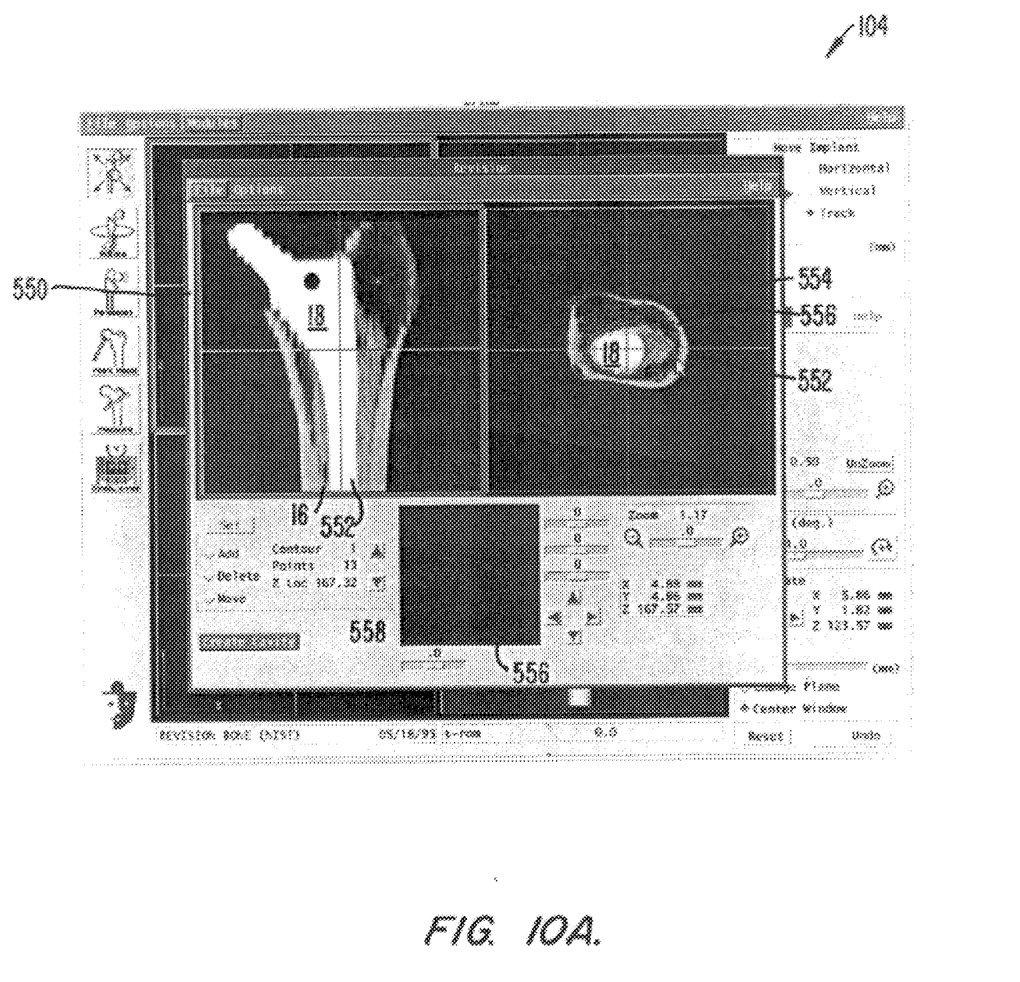
FIGS. 10A–10D are screen displays showing a definition of the cut cavity.

The above has been a general description of steps that may be performed to generate the plan files for creating a new femoral cavity. In order to illustrate some of these steps more clearly, FIGS. 10A–10D are screen displays showing a definition of the cut cavity. FIG. 10A shows screen display 104 with a cross-sectional front view window 550. In window 550, femur 16 has implanted femoral prosthesis 18 (as described in reference to FIG. 1). Around the femoral prosthesis, at varying thicknesses, is bone cement 552 to anchor the femoral prosthesis in the femoral cavity. Window 550 also includes the x and z axes as shown. For identification purposes in the different views, the horizontal axis in the front view will be called the x-axis, the axis perpendicular to the cross-sectional view (not shown) will be called the y-axis and the vertical axis will be called the z-axis.

A transverse view window 554 shows a transverse view of the femur. In the transverse view, femoral prosthesis 18 is surrounded by bone cement 552 which interfaces with femur 16. Approximately thirteen points (indicated by small circles and one indicated by the arrow icon) define the bounding contour at this axial location (i.e., the axial location defined by the x-axis in window 550). The system generates the bounding contour according to the points (e.g., may be done by connecting the points). Window 554 also includes the x and y axes.

A 3D model view window 556 shows the cut cavity in a 3D perspective. The system contour at the current location is highlighted at 558 as shown. In FIG. 10A, the user has defined a first bounding contour at a selected axial location.

Figure 10B:
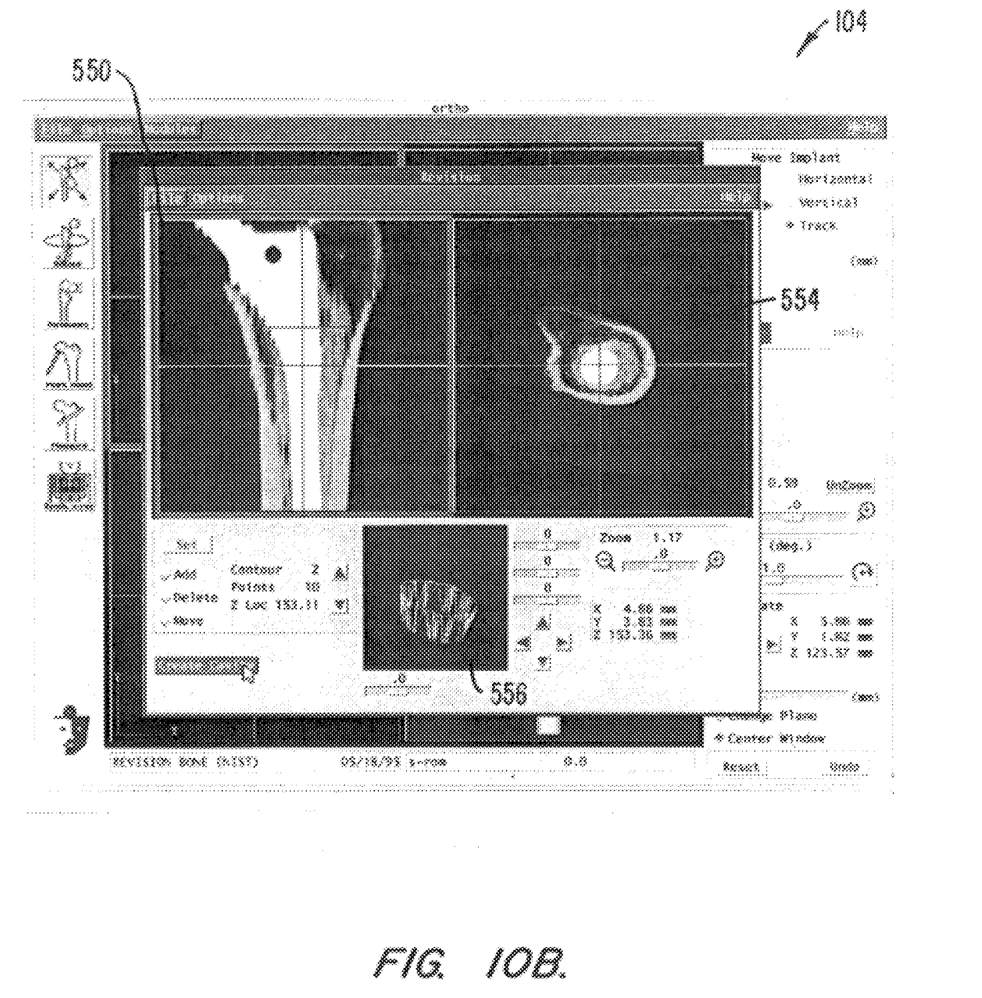

FIG. 10B shows screen display 104 where the user has defined a second bounding contour at a second axial location indicated by the x-axis. The screen display shows cross-sectional front view window 550, transverse view window 554, and 3D model view window 556. Window 554 shows the new bounding contour and window 556 shows the cut cavity in a 3D perspective.

Figure 10C:
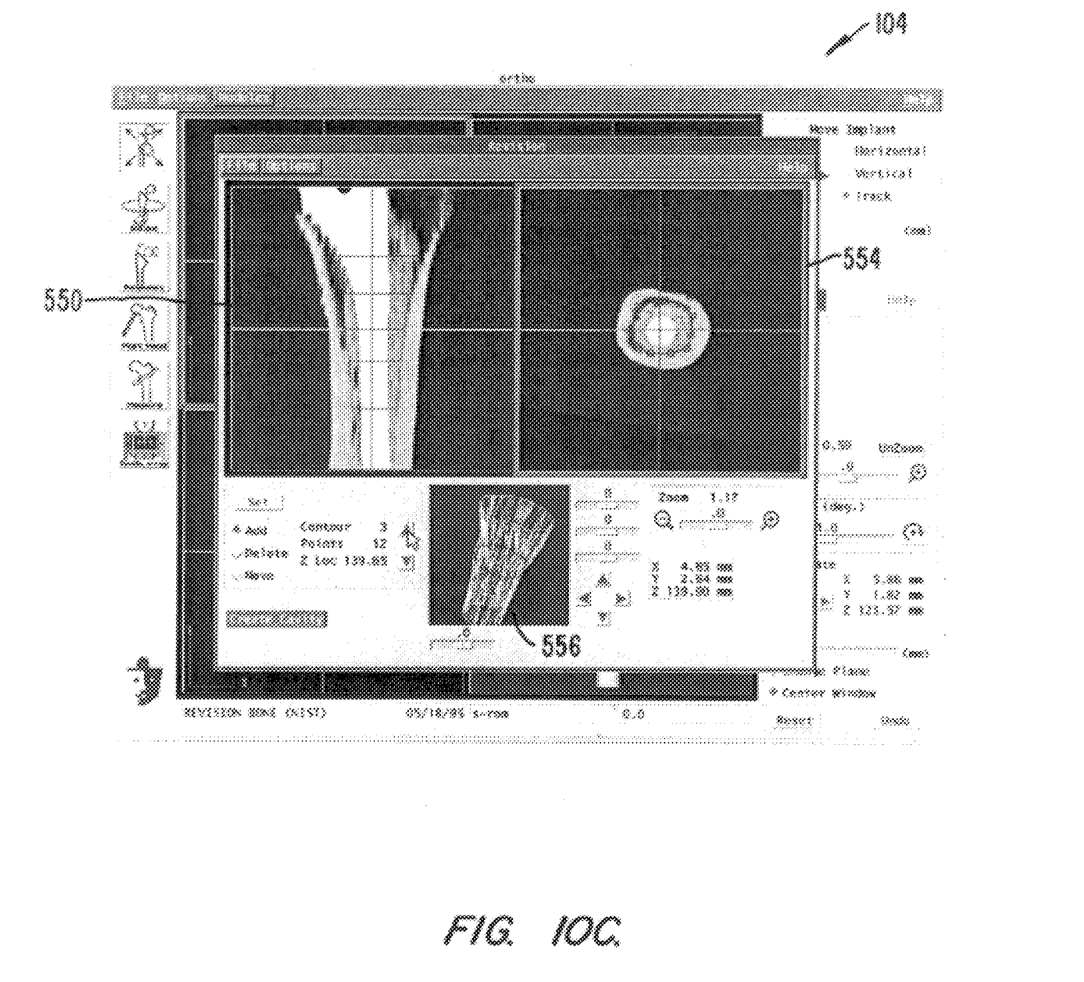

FIG. 10C shows screen display 104 with cross-sectional front view window 550, transverse view window 554, and 3D model view window 556 after the user has defined five bounding contours. Window 556 shows the cut cavity in a 3D perspective.

Figure 10D:
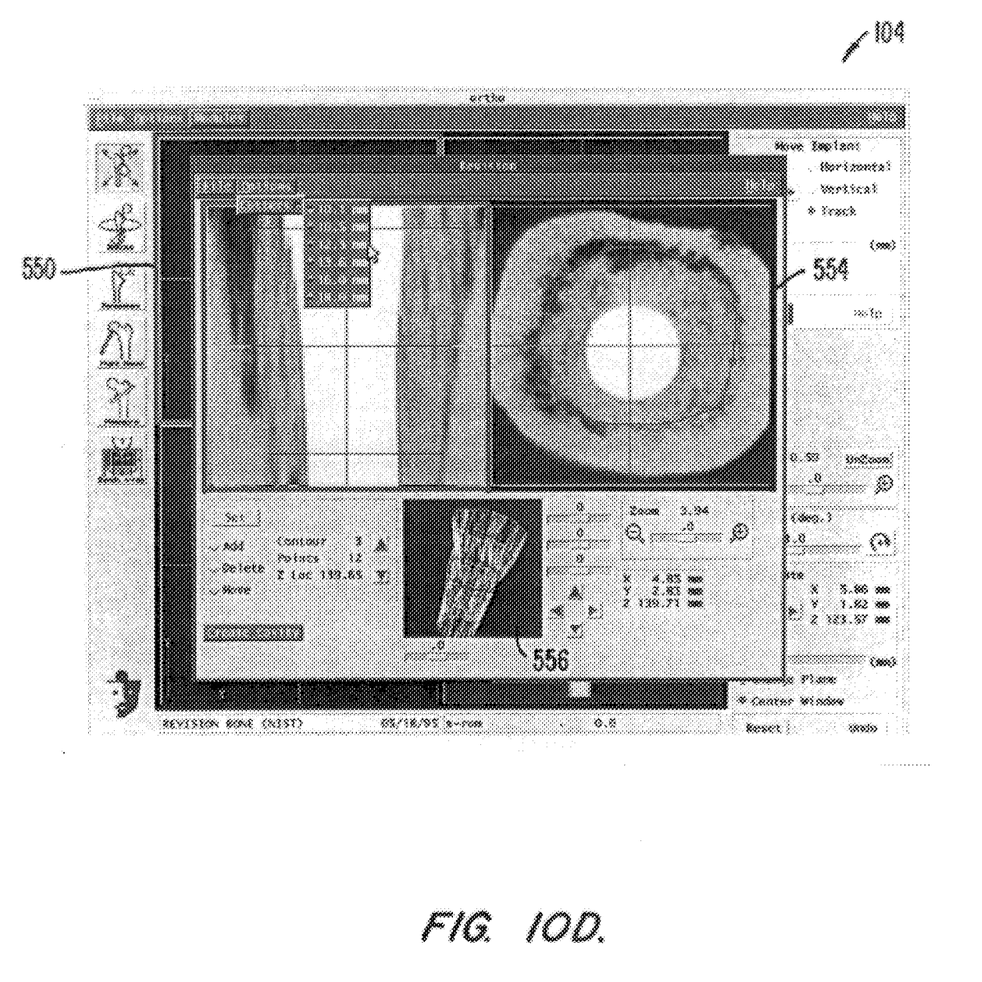

FIG. 10D shows a screen display similar to FIG. 10C except that the user has zoomed-in on front view window 550 and transverse view window 554. Additionally, the user is utilizing a pull-down menu to select the size of the cutting tool that will be utilized to cut the cavity. The system will utilize the size of the cutting tool to generate the system contours.

Figure 11:
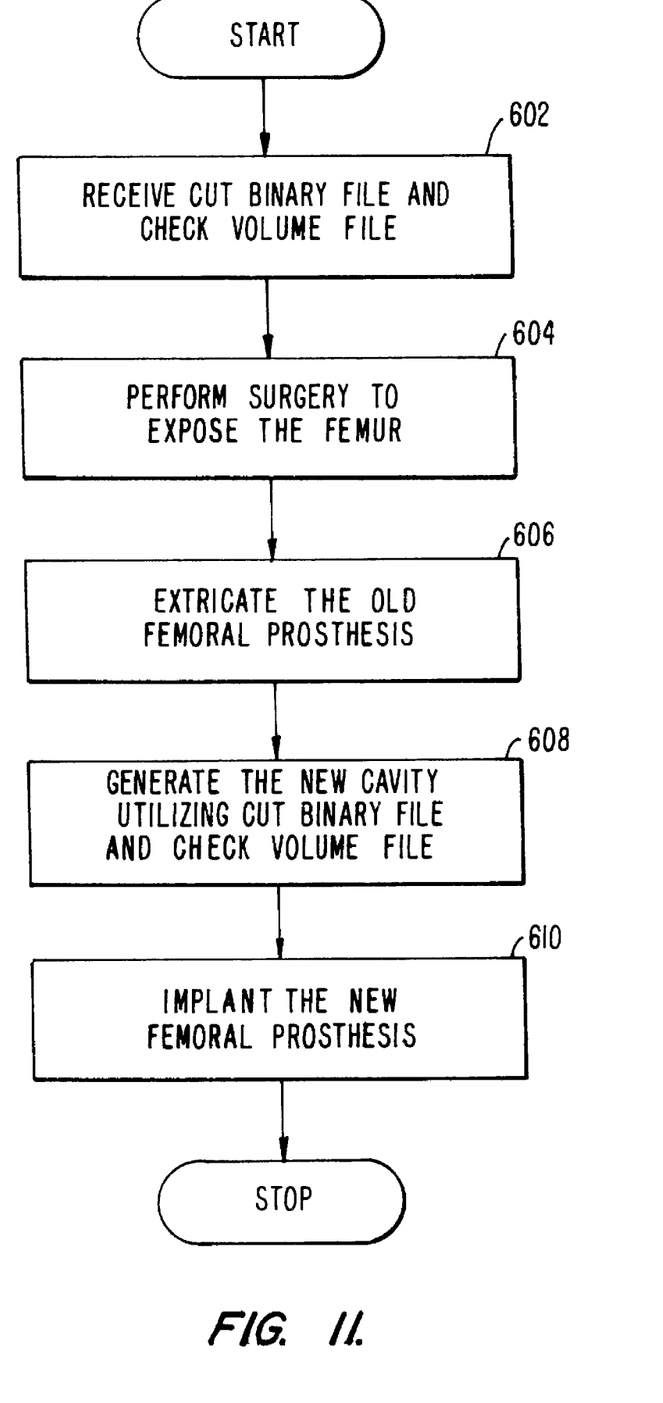
FIG. 11 shows a flowchart of a process of replacing the old femoral prosthesis with a new prosthesis.

FIG. 11 shows a flowchart of a process of replacing the old femoral prosthesis with a new prosthesis. For simplicity, the following will only briefly describe the process of replacing the femoral prosthesis. The replacement of the acetabular cup will not be described but may be performed by conventional methods or utilizing the principles of the present invention.

At step 602, the surgical robot system receives the plan files including the cut binary file and check volume file. Although the computer system for presurgical planning workstation and the surgical robot system may be the same computer, in a preferred embodiment they are different computers as one is in the ORTHODOC™ presurgical planning workstation and one is in the ROBODOC™ surgical robot system.

In the operating room, the surgeon performs the conventional surgery to expose the femur at step 604. Once the femur is exposed, the surgeon extricates or removes the old femoral prosthesis at step 606. The method utilized to remove the old implant may vary depending on a number of factors. However, one method involves striking the prosthesis with a mallet or hammer to disengage the bone cement. Then, the surgeon may use a hand tool like a steel punch, vice-grip-type device, and the like to remove the prosthesis.

At step 608, the surgical robot is attached to the femur to generate or machine the new cut cavity. The surgical robot utilizes the location of metallic pins on the femur to resister the femur to the CT scan data. Once the surgical robot is positioned to cut the cavity, the surgeon may instruct the surgical robot to cut the cavity defined in the binary cut file. The check volume file provides a safety mechanism such that the surgical robot is deactivated if the cavity being machined differs from the cavity that was designed on the presurgical planning workstation. The general procedure of utilizing a surgical robot to cut a cavity in the femur is described in more detail in the references cited above describing the ROBODOC™ surgical robot system.

The new femoral prosthesis is implanted at step 610. After the new prosthesis has been implanted, the surgeon closes the patient.

While the above is a complete description of specific embodiments of the invention, various modifications, alternative constructions, and equivalents may be used. For example, the present invention may also be utilized in other surgical procedures to replace a bone prosthesis as in knee replacement surgery. Additionally, the bounding contours may be defined to remove materials other than bone cement. Therefore, scope of the invention should be determined not with reference to the above description, but instead should be determined with reference to the appended claims along with their full scope of equivalents.

What is claimed is:

1. A method for producing a cut file useful for controlling a robotic system for replacing a bone prosthesis, said method comprising the steps of:

receiving image data comprising an image of a bone;

identifying bounding contours of a non-bone material surrounding a first bone prosthesis to be removed in the image data;

generating system contours from the bounding contours, the system contours specifying a cavity to be cut in the bone to accommodate a second bone prosthesis;

generating a cut file from the system contours for use by the robotic system; and storing the cut file in a tangible medium.

2. The method of claim 1, wherein the bounding contours specify a plurality of regions at varying depths.

3. The method of claim 2, wherein the step of generating the system contours from the bounding contours includes the step of enlarging a region at a depth to allow the cavity to be cut.

4. The method of claim 1, further comprising the step of generating a check file that specifies desired characteristics of the cavity.

5. The method of claim 1, further comprising the step of verifying that the second bone prosthesis is insertable in the cavity.

6. The method of claim 1, further comprising the step of receiving input from a user to select the second bone prosthesis from a plurality of prostheses.

7. The method of claim 1, further comprising the step of displaying on a display screen a plurality of cross-sectional views of the bone.

8. The method of claim 7, further comprising the step of displaying the bounding contours and system contours on the plurality of cross-sectional views.

9. The method of claim 8, further comprising the step of receiving input from a user to generate a cross-sectional view at a desired location.

10. The method of claim 1, further comprising the step of displaying on a display screen a three-dimensional model of the cavity.

11. The method of claim 1, further comprising the step of receiving input from a user to modify the bounding contours.

12. A computer program product for replacing a bone prosthesis, comprising:

computer readable code for receiving image data of a bone;

computer readable code for identifying bounding contours of a non-bone material in the image data, wherein said material surrounding a first bone prosthesis for removal;

computer readable code for generating system contours from the bounding contours, the system contours specifying a cavity to be cut in the bone to accommodate a second bone prosthesis;

computer readable code for generating a cut file from the system contours; and a tangible medium for storing the computer readable codes.

\* \* \* \* \*